United States Patent [19]

Amdur et al.

[11] Patent Number: 5,458,588
[45] Date of Patent: Oct. 17, 1995

[54] LATEX COMPOSITIONS AND ARTICLES MANUFACTURED THEREFROM

[75] Inventors: Shimon Amdur, Highland Park; Warren J. Hintz, Colts Neck; Robert E. Lauer, Trenton, all of N.J.

[73] Assignee: Carter-Wallace Inc., New York, N.Y.

[21] Appl. No.: 221,485

[22] Filed: Jul. 19, 1988

[51] Int. Cl.⁶ .......................... A61F 13/15; A41D 19/00; C08K 3/34
[52] U.S. Cl. ................. 604/349; 2/168; 524/493
[58] Field of Search ............... 524/493; 604/349; 2/168

[56] References Cited

U.S. PATENT DOCUMENTS

| | | | |
|---|---|---|---|
| 2,371,883 | 3/1945 | Gammeter | 604/349 |
| 2,392,049 | 1/1946 | Kinnucan | 604/349 |
| 2,806,012 | 9/1957 | Allen | 524/493 |
| 2,807,600 | 9/1957 | Newton | 524/493 |
| 2,898,391 | 8/1959 | Wagner | 524/493 |
| 4,267,092 | 5/1981 | Glaser | 524/493 |
| 4,585,826 | 4/1986 | Graves | 524/493 |

*Primary Examiner*—Peter D. Mulcahy
*Attorney, Agent, or Firm*—Kevin B. Clarke

[57] ABSTRACT

Liquid mixtures containing natural rubber latex and aqueous dispersions of hydrophillic fumed silica useful in the manufacture of dipped latex goods characterized by improved tensile strength, wet strength, break force, puncture and tear properties are disclosed.

7 Claims, No Drawings

LATEX COMPOSITIONS AND ARTICLES MANUFACTURED THEREFROM

This invention relates to novel compositions containing natural rubber latex. More particularly, this invention is concerned with improving the properties of natural rubber latex compositions and cured sheath goods such as condoms, gloves, etc. produced from such compositions using dip molding techniques. Specifically, this invention is concerned with improving the properties of dipped vulcanized natural rubber latex goods. More specifically, this invention is concerned with improving the tensile strength, wet strength, break force, puncture and tear properties of condoms produced from latex without increasing the thickness of the condom and consequent loss of sensitivity to the user.

There has developed around natural rubber latex a substantial industry for producing such articles as condoms, rubber gloves, surgical supplies, balloons, bathing caps and countless other articles. The articles are generally produced by dipping glass, porcelain or metal forms into natural rubber latex baths and subsequently coagulating and curing the thin film of latex which adheres to the form. Thicker films are obtained by repeating the dipping, coagulating and curing operations as desired. The films are then usually stripped from the molds and optionally may be further cured at elevated temperatures.

Natural rubber laticies are particularly useful in dipping operations, since, unlike synthetic rubber laticies such as chloroprene polymers (neoprene rubber), butadiene-styrene copolymers (Buna S rubber) or butadiene-acrylonitrile copolymers (Buna N rubber), natural rubber latex in its membranous form possesses a very high degree of wet film strength.

As used herein, the term "natural rubber" refers to elastomeric substances obtained from trees or plants such as the quayule and the hevea rubber trees usually by directly tapping the trees by means of cuts into the bark of the tree. The fluid which flows from the tree is not a part of the tree's sap but is natural rubber latex. The latex is made up of individual particles varying in size from between about 0.005 and 2.5 microns. Chemically the particles are stereo-regular polymers of cis-1,4 polyisoprene carrying a negative charge with an isoelectric point in about the 4–5 pH range.

Natural rubber latex is subject to putrification and coagulation within a few hours of collection unless a chemical stabilizer and/or preservative is added to the latex. As a practical matter, stabilizers and preservatives such as ammonia or combinations of ammonia and blends of secondary preservatives such as tetramethylthiuram disulfide, which also functions as a vulcanizer and accelerator, and zinc oxide are added directly to containers used in the collection of the latex.

The rubber content of the natural rubber laticies as collected is usually between about 30 to 40 percent by weight. Generally, the laticies are concentrated by one of several well established methods, i.e., heat concentrating, centrifuging or creaming to produce laticies having a rubber content of from about 60 to 75 percent for commercial use. The laticies employed in the present invention have a rubber content ranging from about 35% to about 65% by weight.

Recently, there has been an increased interest in the production of condoms from natural rubber latex formulations and an effort has been undertaken by the industry to improve the properties of such dipped latex articles. Moreover, numerous attempts have been made to design and improve condoms in order to provide greater protection against contraception and/or against the transfer of infectious matter than may be provided by the standard condom.

Normally the condom is made of strong, fine rubber, or some type of fine animal skin or a synthetic membrane. Of necessity, in order to provide an acceptable level of tactile stimulation to the wearer, the condom must be quite thin. In general, it is elastically fitted to the male organ and during coitus remains stretched and taut. This stretched, taut condition can increase the hazard of the condom being torn or bursting during use.

In accordance with the present invention, methods have now been found for improving the properties of vulcanized sheath rubber articles produced from natural rubber laticies by the addition to such laticies of hydrophillic fumed silica suspensions whereby the tensile strength, tear strength, wet strength, break force and puncture resistance of vulcanized dipped latex goods, including without limitation condoms and gloves, prepared from such improved rubber laticies are obtained.

Methods are known in the prior art for preparing liquid mixtures in the manufacture of latex goods, for instance a water solution of a resorcinol-formaldehyde resin prepared by the interaction between formaldehyde and resorcinol is mixed with carbon black in a colloid mill, after which the carbon black/resin mixture is mixed with latex in a mixer at a pressure of from 35 to 560 Kg./sq. cm. The mixtures cannot be prepared unless the formaldehyde-resorcinol resin is present and the presence of the water soluble formaldehyde-resorcinol resin in the latex formulations impairs the properties of the latex and of the dipped articles subsequently produced. In addition, the method is expensive in that the formaldehyde-resorcinol resins must be purchased or produced and high pressures must be maintained in order to obtain adequate mixing of the carbon black/resin mixture with the latex.

U.S. Pat. No. 3,297,780 discloses rubber products having high tear resistance formed from rubber stock in which a rubber-immiscible liquid in the form of discrete droplets is uniformly dispersed throughout the rubber stock.

U.S. Pat. No. 3,774,885 discloses a method of preparing synthetic chloroprene rubber latex (neoprene) mixtures including carbon black, kaolin or aerosil (silica) filling materials without the use of emulsifiers, such as water soluble formaldehyde-resorcinol resin emulsifying agents, which requires a complex multistep process of bringing together the components of the mixture and mixing the same with the aid of ferromagnetic objects upon which a rotating electromagnetic field acts, with subsequent separation of said ferromagnetic objects from the prepared mixtures.

U.S. Pat. No. 4,585,826 discloses natural rubber formulations, exhibiting increased tear strength, and hardness properties, which contain certain carboxy-terminated butadiene-acrylonitrile copolymers.

It has now been found that mixtures of natural rubber latex and the reinforcing component, silica, can be prepared by combining an aqueous dispersion of silica with the natural rubber latex without the use of emulsifying agents or the use of ferromagnetic objects or electromagnetic fields.

A water-insoluble solid material, such as silica, when it is to function as a latex phase modifier must be converted to a water-compatible system in order to be uniformly combined into the latex system without upsetting the delicate balance of the latex system.

This is accomplished by preparing the silica as an aqueous dispersion of fumed silica. In preparing such dispersions the silica, water and compounding agents such as dispersing agents, wetting agents, thickening agents, colloidal stabilizers etc. are combined in a suitable mill such as a pebble mill, ball mill, colloid mill, attrition mill or ultrasonic disperser and ground for an extended period of time, i.e., twenty-four hours. The resulting silica dispersion has a particle size in the range of about 0.007 to about 5.0 microns. In the present invention, a preferred silica dispersion is that marketed commercially by The Cabot Corporation under the tradename CAB-O-SPERSE.

Moreover, the use of suspensions or dispersions of hydrophillic fumed silica in combination with natural rubber latex in dipping operations for the preparation of natural latex goods, including without limitation, condoms and gloves, yields dipped goods having markedly improved tensile strength, tear strength, wet strength, puncture resistance and break force properties without increasing the thickness of the final product and consequent loss of sensitivity for the user.

The latex compositions of the present invention are prepared by combining an aqueous dispersion of hydrophillic fumed silica, wherein the pH of the dispersion has been adjusted to above about 10 such as by the addition of a base which may be concentrated ammonia, potassium hydroxide, and the like, slowly to a natural rubber latex which has been thoroughly mixed and mixing the latex/silica combination until viscosity stabilizes, i.e., on the order of from about 0.5 to about 16 hours. While not being bound by any theory, it is believed that the base reacts with the fatty acids present in the latex to produce an anionic soap which acts as a colloidal or anionic stabilizer for the latex thus permitting the addition of hydrophillic fumed silica to the latex without disruption of the delicate latex balance. The presence of this stabilizing effect prevents the premature coagulation of the latex and formation of prefloc during compounding and processing of the latex.

In addition, as is well known in the art, other materials, commonly known as "rubber chemicals", that impart particularly desired properties to the finished dipped goods may be added to the latex, i.e., curing, cross-linking or vulcanizing agents such as sulphur, vulcanization accelerators and activators, including metal oxides and hydroxides, i.e., zinc, calcium, sodium and organic accelerators such as the dithio carbamates, xanthates, thiourea, mercapto compounds, etc., antioxidants and other antidegradents in amounts that vary depending on characteristics of the latex, solids content and properties desired.

Preferably, the rubber chemicals employed, if not water soluble, are of a partical size approximately equal to the rubber particle size in the latex. Moreover, water insoluble materials should be emulsified or dispersed in water prior to blending or mixing into the latex. The compounding of the rubber chemicals and latex takes place under ambient conditions, preferably at about 75° F. after which the mixture is aged or stored for about twenty-four hours. The amount of hydrophillic fumed silica subsequently added to the mixture is from about 0.5 to about 15 parts per 100 parts rubber in the natural rubber latex. Preferably about 5 parts hydrophillic fumed silica per 100 parts by weight of natural rubber in the latex.

The proposed method has certain advantages over those heretofore known. The reinforced latex compositions prepared by the method of the present invention produce dipped cured latex sheath goods such as condoms and surgical gloves with physical and mechanical properties superior to those obtained with similar dipped latex goods containing no silica reinforcement.

In a preferred embodiment of the present invention, the novel silica reinforced latex compositions of the present invention are formed into rubber contraceptives, prophylactics or condoms by means well-known to those skilled in the art.

The traditional methods of manufacturing a contraceptive, prophylactic or condom involve the so-called straight dipping or dip and dry techniques wherein a phallic shaped mandrel, normally of ceramic, metal or glass composition, of predetermined size is, optionally coated with a coagulating agent, and dipped into a warm bath containing natural rubber latex. The mandrel when dipped may be stationary or rotating about its longitudinal axis. Optionally, a circumferential groove in the mandrel may be located towards the upper open end of the mandrel. The mandrel, when immersed in the latex bath, is immersed to a depth sufficient to yield the finished condom of desired length plus an additional distance to allow for formation of a latex ring at the open end of the condom or to a depth coincident with the upper edge of the circumferential groove which would then form the latex ring. After a predetermined period of time the mandrel, covered with a coating of latex which conforms to the mandrel's shape and optionally including the circumferential ring is withdrawn. The latex coating is allowed to dry or is cured at elevated temperatures to form a latex sheath optionally containing a thickened ring of latex formed at its upper open end. Alternatively, the ring or beading may be formed by rolling the sheath on itself for several turns, then curing the sheath and applying an anti-tack agent. Depending on the desired thickness of the latex sheath, the dipping and curing operation may be repeated one or more additional times. Optionally upon completion of the final cure the formed latex sheath may be coated with an anti-tack material such as talc, microporous solid particles, lubricants, slip agents, spermicides, deodorants, etc., prior to removal from the mandrel.

After completion of the dipping, curing and optional coating steps, the sheath is removed from the mandrel by starting from the upper portion of the latex sheath and rolling the sheath off the mandrel surface around the thickened latex ring or bead to form a cup-shaped elastic ring of predetermined size and circumference. The result is several layers of latex being rolled around the thickened latex ring formed at the top, open end, of the sheath forming a cup within the circumference of the ring. In this form, the prophylactic sheath is easily mountable for use during sexual intercourse. At this point, additional lubricants, spermacides, bacteriacides, etc., may also be added to the cup-shaped latex sheath.

For a more complete understanding of the invention by those skilled in the art, the following examples are given by way of illustration.

EXAMPLE 1

PREPARATION OF LATEX DIPPING BATH—35 GRAIN CONDOM

A homogeneous stable latex composition is prepared by stirring 2.0 parts by weight zinc oxide, 0.1 parts by weight potassium hydroxide, 0.1 parts by weight sodium dibutyldithiocarbamate and 0.5 parts by weight dispersed sulfur into ammonia preserved 46% solids content natural rubber latex. Mixing was continued for 12 hours and the mixture stored in drums for twenty-four hours.

Condoms (35 grain) were dipped from this latex bath using well-known dipping and curing procedures as hereinabove set forth.

EXAMPLE 2

PREPARATION OF LATEX DIPPING BATH—22 GRAIN CONDOM

The procedure of example 1 was repeated and the volume of the resulting latex composition was increased by the addition of deionized water with mixing to a latex solids content of 42%.

Condoms (22 grain) were dipped from this latex bath.

EXAMPLE 3

PREPARATION OF SILICA REINFORCED DIPPING BATH—35 GRAIN CONDOM

The procedure of example 1 was repeated. And, 200 pounds of an aqueous dispersion of silica 17.8 weight % solids content was stabilized with ammonia to a pH of 10.0 One hundred eighty three (183) pounds of the stabilized silica dispersion was blended into the latex mixture and stirred for 2.5 hours.

Thirty five (35) grain silica reinforced condoms were prepared from the bath by dipping.

EXAMPLE 4

PREPARATION OF SILICA REINFORCED DIPPING BATH—22 GRAIN CONDOM

The procedure of example 3 was repeated and the volume of the resulting silica reinforced latex composition was increased by the addition of deionized water with mixing to a latex solids content of 42%.

Twenty two (22) grain silica reinforced condoms were prepared from the bath by dipping.

The following tables demonstrate the superior physical properties of silica reinforced condoms prepared in accordance with the present invention as compared to condoms prepared from non-reinforced latex compositions.

TABLE I

Detailed experimental results for 35 grain condoms produced from the latex bath of example 1.
CPR PHYSICAL TESTING LABORATORY
CONDOM RING TEST
ASTM D - 3492-83

| Sample Number | Mean Thickness (0.000") | Tensile @ 600% (MPa) | Tensile @ Break (MPa) | Force @ Break (N) |
|---|---|---|---|---|
| 1 | 3.63 | 9.10 | 15.56 | 57.40 |
| 2 | 3.61 | 9.18 | 17.50 | 64.09 |
| 3 | 3.65 | 8.49 | 18.01 | 66.66 |
| 4 | 3.16 | 10.41 | 22.94 | 73.67 |
| 5 | 3.62 | 9.34 | 15.52 | 57.02 |
| 6 | 3.81 | 9.45 | 22.76 | 87.94 |
| 7 | 3.44 | 8.87 | 14.97 | 52.24 |
| 8 | 3.63 | 9.18 | 20.86 | 76.96 |
| 9 | 3.52 | 9.89 | 20.30 | 72.48 |
| 10 | 3.53 | 9.22 | 13.08 | 47.87 |
| MEANS = | 3.56 | 9.31 | 18.15 | 65.53 |
| STD DEV. = | 0.17 | 0.53 | 3.43 | 12.53 |

TABLE II

Detailed experimental results for silica filled 35 grain condoms produced from the latex bath of example 3.
CPR PHYSICAL TESTING LABORATORY
CONDOM RING TEST
ASTM D - 3492-83

| Sample Number | Mean Thickness (0.000") | Tensile @ 600% (MPa) | Tensile @ Break (MPa) | Force @ Break (N) |
|---|---|---|---|---|
| 1 | 3.60 | 13.00 | 32.37 | 118.20 |
| 2 | 3.28 | 15.97 | 27.98 | 93.26 |
| 3 | 3.23 | 16.19 | 29.80 | 97.73 |
| 4 | 3.47 | 16.36 | 22.94 | 80.90 |
| 5 | 3.41 | 16.04 | 30.13 | 104.40 |
| 6 | 3.44 | 14.51 | 28.01 | 97.73 |
| 7 | 3.43 | 16.88 | 24.57 | 85.49 |
| 8 | 3.36 | 14.74 | 25.92 | 88.51 |
| 9 | 3.26 | 16.19 | 31.76 | 105.00 |
| 10 | 3.43 | 15.99 | 29.58 | 102.90 |
| MEANS = | 3.39 | 15.59 | 28.31 | 97.41 |
| STD DEV. = | 0.11 | 1.16 | 3.06 | 10.96 |

TABLE III

Detailed experimental results for 22 grain condoms produced from the latex bath of example 2.
CPR PHYSICAL TESTING LABORATORY
CONDOM RING TEST
ASTM D - 3492-83

| Sample Number | Mean Thickness (0.000") | Tensile @ 600% (MPa) | Tensile @ Break (MPa) | Force @ Break (N) |
|---|---|---|---|---|
| 1 | 2.14 | 11.80 | 23.84 | 51.80 |
| 2 | 2.31 | 11.81 | 12.02 | 28.19 |
| 3 | 2.40 | 12.08 | 19.46 | 47.35 |
| 4 | 2.37 | 11.52 | 24.18 | 58.15 |
| 5 | 2.54 | 11.85 | 29.01 | 74.90 |
| 6 | 2.12 | 11.78 | 28.40 | 61.02 |
| 7 | 2.23 | 12.04 | 22.36 | 50.63 |
| 8 | 2.26 | 12.40 | 23.80 | 34.69 |
| 9 | 2.41 | 11.64 | 19.22 | 47.02 |
| 10 | 2.16 | 11.29 | 25.20 | 55.17 |
| MEANS = | 2.29 | 11.82 | 22.75 | 52.90 |
| STD DEV. = | 0.14 | 0.31 | 4.94 | 11.87 |

TABLE IV

Detailed experimental results for silica filled 22 grain condoms produced from the latex bath of example 4.
CPR PHYSICAL TESTING LABORATORY
CONDOM RING TEST
ASTM D - 3492-83

| Sample Number | Mean Thickness (0.000") | Tensile @ 600% (MPa) | Tensile @ Break (MPa) | Force @ Break (N) |
|---|---|---|---|---|
| 1 | 2.24 | 15.80 | 30.39 | 69.11 |
| 2 | 2.52 | 16.83 | 31.91 | 81.64 |
| 3 | 2.43 | 14.73 | 30.75 | 75.76 |
| 4 | 2.24 | 14.57 | 30.59 | 69.67 |
| 5 | 2.32 | 16.57 | 29.91 | 70.45 |
| 6 | 2.10 | 14.11 | 27.26 | 58.21 |
| 7 | 2.40 | 14.79 | 34.13 | 83.17 |
| 8 | 2.27 | 15.39 | 30.22 | 69.55 |
| 9 | 2.15 | 14.09 | 28.92 | 63.23 |
| 10 | 2.31 | 14.80 | 28.83 | 67.61 |
| MEANS = | 2.30 | 15.17 | 30.29 | 70.84 |
| STD DEV. = | 0.13 | 0.96 | 1.86 | 7.65 |

TABLE V

Physical Properties of Condoms Produced as a Function of Silica Addition from Zero to about 5 Parts Per 100 Parts Rubber
MEAN DATA - RING TEST
(MEANS 10)
ASTM D - 3492-83

| Sample | Thickness (000") | MPa @ Break | Break (newtons) | Elongation (%) |
|---|---|---|---|---|
| Example 2 | 2.63 | 23.13 | 61.61 | 807.9 |
| 1. 1 Part Silica | 2.62 | 23.23 | 61.66 | 787.9 |
| 2. 1 Part Silica | 2.69 | 23.18 | 63.31 | 755.4 |
| 3. 2 Part Silica | 2.58 | 27.24 | 71.21 | 795.9 |
| 4. 2 Part Silica | 2.56 | 27.93 | 72.50 | 764.7 |
| 5. 3 Part Silica | 2.72 | 31.44 | 86.78 | 783.6 |

TABLE VI

Evaluation of Tear and Puncture Properties of Silica Added Condoms and Non-reinforced Condoms

| PRODUCT | BREAK FORCE (Pounds) | FORCE PER INCH (Pounds) |
|---|---|---|
| TEAR INITIATION (TEAR RESISTANCE TO START) ASTM D - 1004-66 | | |
| Example 3 | .72 | 331.73 |
| Example 1 | .60 | 297.39 |
| TEAR PROPAGATION (TEAR RESISTANCE TO CONTINUE) ASTM D - 1938-67 | | |
| Example 3 | .406 | 171.67 |
| Example 1 | .234 | 124.00 |

| PRODUCT | PUNCTURE FORCE (Pounds) | FORCE PER INCH (Pounds) |
|---|---|---|
| PUNCTURE TEST ASTM D - 120-84a | | |
| Example 3 | 2.76 | 958 |

TABLE VI-continued

Evaluation of Tear and Puncture Properties of Silica Added Condoms and Non-reinforced Condoms

| | | |
|---|---|---|
| Example 1 | 1.76 | 669 |

Although the invention has been described with respect to specific modifications, the details thereof are not to be construed as limitations, for it will be apparent to those skilled in the art that various equivalents, changes and modifications may be resorted to without departing from the spirit and scope thereof and it is understood that such equivalent embodiments are intended to be included therein.

What is claimed is:

1. Flexible dipped rubber articles selected from the group consisting of gloves and condoms characterized by superior tensile strength, wet strength and resistance to tearing, breaking and puncture formed from a composition consisting essentially of a dispersion of hydrophillic fumed silica having a particle size of from about 0.007 to about 5.000 microns in natural rubber latex.

2. Flexible rubber articles according to claim 1 which are prepared by dipping.

3. A condom as claimed in claim 2 wherein said natural rubber latex has a rubber solids content of from about 35% to about 65% by weight.

4. A condom as claimed in claim 2 wherein the ratio of silica to rubber solids in said cured composition is from about 0.5 to about 15 parts by weight silica per about 100 parts by weight rubber solids.

5. A condom as claimed in claim 4 wherein said silica is present in amounts of from about 5 parts by weight per about 100 parts by weight rubber solids.

6. A condom as claimed in claim 2 wherein said silica is a hydrophillic fumed silica having a particle size of from about 0.007 to about 5.0 microns.

7. A condom as claimed in claim 6 wherein said silica has a particle size of from about 0.1 to about 5.0 microns.

* * * * *